US00PP24151P2

(12) United States Plant Patent
Bentley

(10) Patent No.: US PP24,151 P2
(45) Date of Patent: Jan. 7, 2014

(54) ***SALVIA* PLANT NAMED 'EGGBEN005'**

(50) Latin Name: *Salvia greggii×microphylla*
Varietal Denomination: EGGBEN005

(76) Inventor: Howard Bentley, Wonga Park (AU)

( * ) Notice: Subject to any disclaimer, the term of this patent is extended or adjusted under 35 U.S.C. 154(b) by 130 days.

(21) Appl. No.: 13/506,155

(22) Filed: Mar. 30, 2012

(51) Int. Cl.
*A01H 5/00* (2006.01)

(52) U.S. Cl.
USPC ..... Plt./475

(58) Field of Classification Search
USPC ..... Plt./475
See application file for complete search history.

*Primary Examiner* — Wendy C Haas
(74) *Attorney, Agent, or Firm* — Cassandra Bright

(57) ABSTRACT

A new and distinct *Salvia* cultivar named 'EGGBEN005' is disclosed, characterized by a dense, bushy plant habit, dark red-purple colored flowers, dark colored calyx and a rigid inflorescence. The new variety is a *Salvia*, normally produced as an outdoor garden or container plant.

2 Drawing Sheets

Latin name of the genus and species: *Salvia greggii×microphylla.*

Variety denomination: 'EGGBEN005'.

BACKGROUND OF THE INVENTION

The new *Salvia* cultivar is a product of a planned breeding program conducted by the inventor, Howard Bentley, in Wonga Park, Victoria, Australia. The objective of the breeding program was to produce new *Salvia* varieties with denser plant habits, strong garden performance, in a range of flower colors.

Between January and March 2003, an assorted range of unpatented, unnamed *Salvia greggii* varieties were pollinated by the unpatented variety *Salvia microphylla* 'San Carlos Festival'. The seeds from these crossing was bulk collected, sown and raised. The new variety was identified as a potentially interesting selection in October 2003, at a research greenhouse in Wonga Park, Australia. Further observations and evaluations were made during 2004.

Asexual reproduction of the new cultivar 'EGGBEN005' by vegetative cuttings was first performed during 2004, at a research greenhouse in Wonga Park. Subsequent propagation has shown that the unique features of this cultivar are stable and reproduced true to type on successive generations.

SUMMARY OF THE INVENTION

The cultivar 'EGGBEN005' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EGGBEN005' These characteristics in combination distinguish 'EGGBEN005' as a new and distinct *Salvia* cultivar:

1. Bushy plant habit.
2. Dark red-purple flower color.
3. Dark calyx coloration.
4. Strong, rigid inflorescence.
5. Dense plant habit.

PARENT COMPARISON

Plants of the new cultivar 'EGGBEN005' are similar to plants of the assorted seed parent cultivars used in the crossing, in most horticultural characteristics, however, plants of the new cultivar 'EGGBEN005' are denser, with a less upright plant habit than any of the observed seed parent cultivars. Additionally, foliage shape of the new cultivar is different than any of the observed seed parent cultivars.

Plants of the new cultivar 'EGGBEN005' are similar to plants of the pollen parent, *Salvia microphyila* 'San Carlos Festival' in most horticultural characteristics, however, plants of the new cultivar 'EGGBEN005' produce more flowers, darker colored calyx, and have a different leaf shape.

COMMERCIAL COMPARISON

Plants of the new cultivar are best compared to the commercial variety *Salvia gregii* 'Red', unpatented. Plants of the new variety produce more flowers per node. Additionally, the varieties differ in leaf shape.

BRIEF DESCRIPTION OF THE PHOTOGRAPHS

Figure 1:
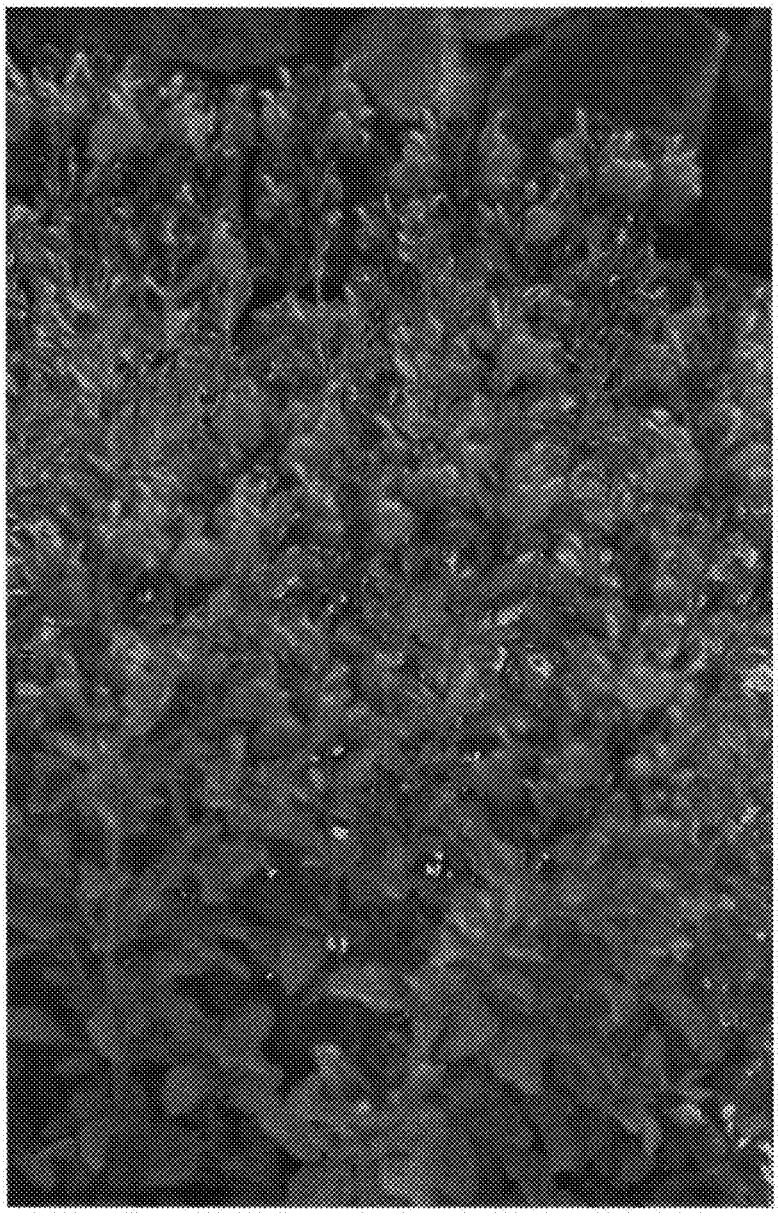

The accompanying photograph in FIG. 1 illustrates in full color a typical flower of 'EGGBEN005'.

Figure 2:
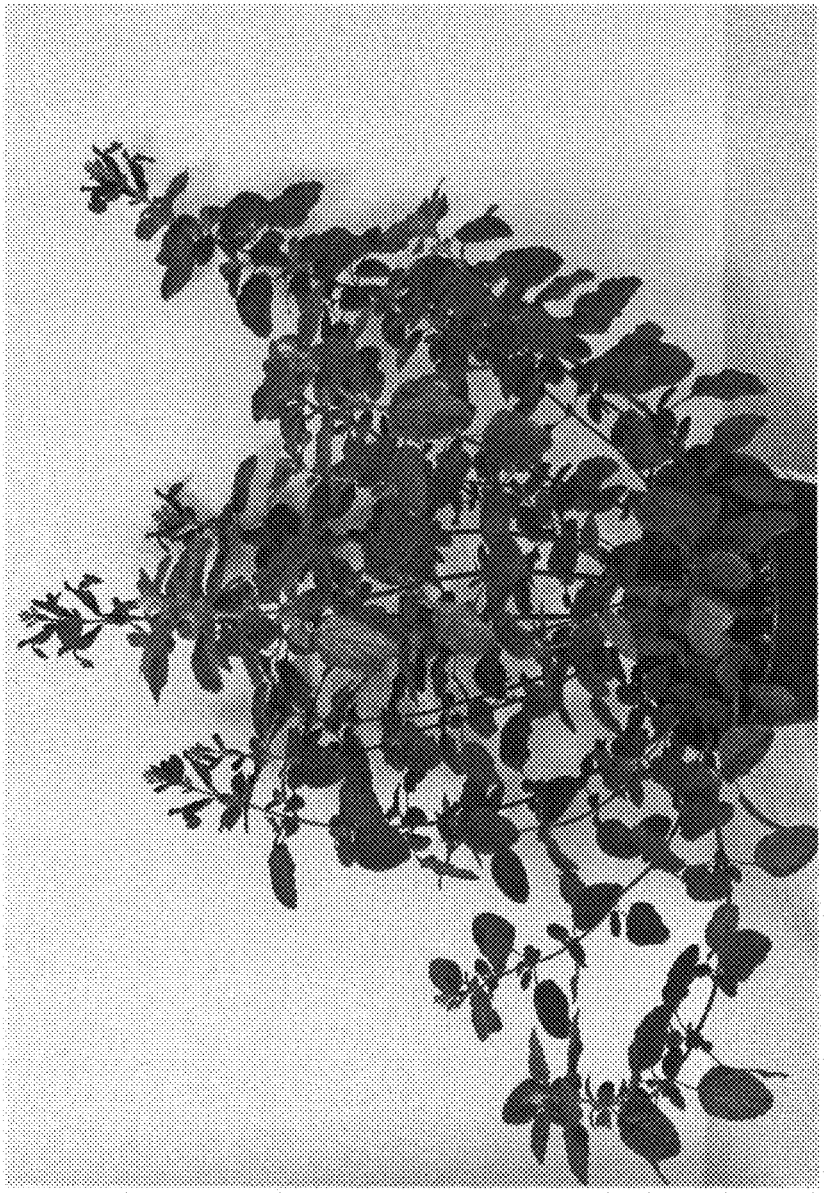

FIG. 2 illustrates in full color a typical plant of 'EGGBEN005' grown in a greenhouse, in Watsonville, Calif., in a commercial 8 inch container. Age of the plant photographed is approximately 20 weeks from an unrooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007 Edition, except where general terms of ordinary dictionary significance are used. The following observations and measurements describe 'EGGBEN005' plants grown in a greenhouse in Watsonville, Calif. The growing temperature ranged from 10° C. to 28° C. The greenhouse is un-shaded, giving bright, normal sunlight conditions. Measurements and numerical values represent averages of typical plant types.

Botanical classification: *Salvia greggii×microphylla* cultivar 'EGGBEN005'.

PROPAGATION

Time to initiate roots: About 5-8 days at approximately 25° C.

Root description: Fine, densely fibrous.

Time to produce a rooted cutting: About 21 days at 25° C.

PLANT

Growth habit: Outwardly arching annual.

Pot size of plant described: 8 inch pot.

Height: Approximately 30 cm to top of foliage. Approximately 40 cm to top of flowering plane. Measured from soil level of pot.

Plant spread: Approximately 48 cm.

Growth rate: Rapid.

Branching characteristics: Free-branching, Approximately 6 primary branches.

Length of primary lateral branches: Approximately 28 cm.

Diameter of lateral branches: Approximately 0.6 cm

Quantity of lateral branches: About 16 to 20.

Stem:

*Color*.—Near RHS Green 137 B. slight flush near Greyed-Purple N186D.

*Pubescence*.—Minute pubescence.

Internode length: Approximately 2.5 to 5.0 cm.

Age of plant described: Approximately 20 weeks from an unrooted cutting.

FOLIAGE

Leaf:

*Arrangement*.—Opposite.

*Quantity*.—Approximately 14 fully expanded per main branch.

*Average length*.—Approximately 6.0 cm., including petiole.

*Average width*.—Approximately 3.1 cm.

*Shape of blade*.—Obovate.

*Apex*.—Obtuse.

*Base*.—Obtuse to nearly truncate.

*Attachment*.—Stalked.

*Margin*.—Crenate.

*Texture of top surface*.—Matte, minute, coarse pubescence.

*Texture of bottom surface*.—Matte, minute, coarse pubescence.

*Color*.—Young foliage upper side: Near RHS Green 137B. Young foliage under side: Near RHS Green 137C. Mature foliage upper side: Near RHS Green 137A. Mature foliage under side: Near RHS Green 138A.

*Venation*.—Type: Pinnate. Venation color upper side: Near RHS Yellow-Green 144A. Venation color under side: Near RHS Green 143C.

*Petiole*.—Average Length: Approximately 1.9 cm. Diameter: Approximately 0.15 cm. Color: Near Yellow-Green 144A.

FLOWER

Natural flowering season: Flowering from early Spring through late Summer.

Inflorescence type and habit: Flowers arranged in verticillasters on spikes.

Flower longevity on plant: Individual flowers last approximately 1 week on the plant. Each spike lasts approximately 7 weeks with flowers.

Quantity of flowers: About 12 buds and 8 fully opened flowers per spike, at one time. Mature plants have approximately 12 to 15 spikes.

Spike size:

*Diameter*.—Approximately 6.5 cm.

*Height*.—Approximately 8 cm.

Individual flowers:

*Size*.—Diameter: Approximately 2.5 cm. Length: Approximately 3.0 cm.

*Persistence*.—Non-persistent.

*Fragrance*.—Very strong, typical *Salvia* scent.

Corolla:

*Petal arrangement*.—The corolla is sympetalous and typically bilabiate with 2 small, highly fused lobes forming an upper lip and 3 larger highly fused lobes forming a lower lip.

*Margin*.—Nearly entire, slightly scalloped.

*Tip shape*.—Upper lip tip retuse, lower lip tip rounded with scallops.

*Length*.—Upper lip Approximately 0.8 cm, lower lip Approximately 1.5 cm. Tube length Approximately 1.8 cm.

*Width*.—Upper lip Approximately 0.5 cm, lower lip Approximately 2.0 cm. Tube width Approximately 0.7 cm.

*Texture*.—Upper lip: highly pubescent on exterior surface. Interior surface glabrous. Lower lip: Glabrous all surfaces.

Color:

*Upper lip*.—When opening: Inner surface: Near RHS Red-Purple 65C. Outer surface: Near RHS Red-Purple 61A. Fully opened: Inner surface: Near RHS Purple 77C. Outer surface: Near RHS Red-Purple 70A. Fading: Inner surface: Near RHS Red-Purple 65C. Outer surface: Near RHS Red-Purple 59B.

Color:

*Lower lip*.—When opening: Inner surface: Near RHS Red-Purple 60A, but much brighter. Outer surface: Near RHS Red-Purple 60B. Fully opened: Inner surface: Near RHS Red-Purple 71A. Outer surface: Near RHS Red-Purple 72B. Fading: Inner surface: Near RHS Red-Purple 61B, but much brighter. Outer surface: Near RHS Red-Purple 61A.

Color:

*Tube*.—When opening: Inner surface: Near RHS Red-Purple 71D. Outer surface: Near RHS Red-Purple 61A. Fully opened: Inner surface: Near RHS Red-Purple 70B. Outer surface: Near RHS Red-Purple 70A. Fading: Inner surface: Near RHS Red-Purple 64A. Outer surface: Near RHS Red-Purple 61A.

Bud:

*Shape*.—Ovoid.

*Length*.—Approximately 1.6 cm.

*Diameter*.—Approximately 0.6 cm.

*Color*.—Near RHS Red-Purple 59A.

Calyx:

*Length*.—Approximately 1.5 cm.

*Diameter*.—Approximately 0.8 cm.

*Shape*.—Tubular.

*Sepals*.—Shape: Quantity per flower: 3, fused to form a tube. Unfused Apex: Length: Approximately 0.6 cm. Width: Approximately 0.5 cm. Margin: Entire. Apex: Acute. Texture: Pubescent. Color: Immature: Near RHS Yellow-Green 144A. Mature: Near RHS Purple N77A.

Peduncle:

*Length*.—Average 2.0 cm.

*Diameter*.—0.35 cm. Color: Near RHS Yellow-Green 144B, occasional thin stripe near Greyed-Purple N186D.

*Orientation*.—Upright, straight.

*Strength*.—Strong.

*Texture*.—Pubescent.

Pedicels:

*Length*.—Average 0.3 cm.

*Diameter*.—0.1 cm Color: Near RHS Yellow-Green 144B, covered almost entirely by flush of Greyed-Purple N186A.

*Orientation*.—Straight, approximately 45 degree angle from attachment.

*Strength*.—Flexible.

*Texture*.—Pubescent.

REPRODUCTIVE ORGANS

Stamens:

*Number*.—2.

*Filament length*.—Approximately 1.5, approximately 1.0 cm of length fused to petal.

*Filament color*.—Near RHS Purple 75D, base Red-Purple 72A.

Anthers:

*Shape*.—Very narrowly elliptic.

*Length*.—Approximately 1 mm.

*Color*.—Near RHS Purple N77A.

*Pollen*.—Moderate, colored near Greyed-Orange 168D.

Pistil:

*Number*.—1.

*Length*.—Approximately 2.6 cm.

*Style*.—Length: Approximately 1.3 cm. Color: Near RHS N155A.

*Stigma*.—Shape: Linear, curled. Color: Near RHS Red-Purple 72A. Ovary color: Near RHS Yellow-Green 144C.

OTHER CHARACTERISTICS

Seeds and fruits: Not observed to date.

Disease/pest resistance: Neither resistance nor susceptibility to pathogens and pests common to *Salvia* have been observed.

Temperature tolerance: The new variety tolerates temperatures between 5 to 35° C.

What is claimed is:

1. A new and distinct cultivar of *Salvia* plant named 'EGGBEN005' as herein illustrated and described.

* * * * *